United States Patent
Bellanova et al.

(10) Patent No.: US 9,148,732 B2
(45) Date of Patent: *Sep. 29, 2015

(54) METHOD FOR TESTING HEARING AIDS

(75) Inventors: Martina Bellanova, Erlangen (DE);
Matthias Latzel, Eggolsheim (DE)

(73) Assignee: Sivantos Pte. Ltd., Singapore (SG)

( * ) Notice: Subject to any disclaimer, the term of this patent is extended or adjusted under 35 U.S.C. 154(b) by 306 days.

This patent is subject to a terminal disclaimer.

(21) Appl. No.: 13/635,723

(22) PCT Filed: Mar. 10, 2011

(86) PCT No.: PCT/EP2011/053600
§ 371 (c)(1),
(2), (4) Date: Nov. 9, 2012

(87) PCT Pub. No.: WO2011/113741
PCT Pub. Date: Sep. 22, 2011

(65) Prior Publication Data
US 2013/0202124 A1    Aug. 8, 2013

(30) Foreign Application Priority Data

Mar. 18, 2010    (DE) .......................... 10 2010 011 950

(51) Int. Cl.
| H04R 29/00 | (2006.01) |
| H04R 25/00 | (2006.01) |
| A61B 5/00 | (2006.01) |
| A61B 5/12 | (2006.01) |

(52) U.S. Cl.
CPC ................ H04R 25/30 (2013.01); H04R 25/70 (2013.01); *A61B 5/002* (2013.01); *A61B 5/121* (2013.01); *A61B 5/7435* (2013.01); *H04R 2225/43* (2013.01)

(58) Field of Classification Search
CPC .......... A61B 5/121; A61B 5/12; H04R 25/70; H04R 25/30; G06F 17/2827; G10L 25/00; G10L 15/10

USPC .............. 381/60; 704/2, 4, 234, 271; 73/585; 600/559, 300

See application file for complete search history.

(56) References Cited

U.S. PATENT DOCUMENTS

| 6,236,964 | B1 * | 5/2001 | Tamura et al. ................ 704/254 |
| 6,651,041 | B1 * | 11/2003 | Juric ............................. 704/228 |
| 6,674,862 | B1 * | 1/2004 | Magilen ......................... 381/60 |
| 2003/0078515 | A1 * | 4/2003 | Menzel et al. ................ 600/559 |
| 2005/0027537 | A1 * | 2/2005 | Krause et al. ................ 704/271 |
| 2006/0093172 | A1 | 5/2006 | Ludvigsen et al. |
| 2011/0264439 | A1 * | 10/2011 | Sata et al. ........................ 704/4 |

OTHER PUBLICATIONS

Boretzki, et al., "The Benefits of Nonlinear Frequency Compression for People with Mild Hearing Loss" Internet citation, Nov. 23, 2009, pp. 1-7, retrieved from URL: http://www.phonak.com/content/dam/phonak/b2b/C_M_tools/Library/Features/SoundRecover/en/NLFC_and_mild_HL_AudiologyOnline_Nov09.pdf.

* cited by examiner

*Primary Examiner* — Vivian Chin
*Assistant Examiner* — Ubachukwu Odunukwe
(74) *Attorney, Agent, or Firm* — Laurence A. Greenberg; Werner H. Stemer; Ralph E. Locher

(57) ABSTRACT

A method for testing hearing aids, particularly in respect of the effect thereof on speech comprehension, is improved. The method has the following steps: a) a test system is provided, b) an audible voice signal in the form of at least one meaningless syllable is selected and presented c) the meaningless syllable and a number of further meaningless syllables are displayed on a graphical user interface in the test system, d) a heard meaningless syllable is selected from the displayed meaningless syllables by the user, e) the selection made is evaluated, and f) method steps c) to e) are repeated until a termination criterion is encountered. The audible voice signal is selected in each case on the basis of at least one selection made by the person in response to a previously presented voice signal. The method allows particularly fast and informative hearing aid tests.

5 Claims, 1 Drawing Sheet

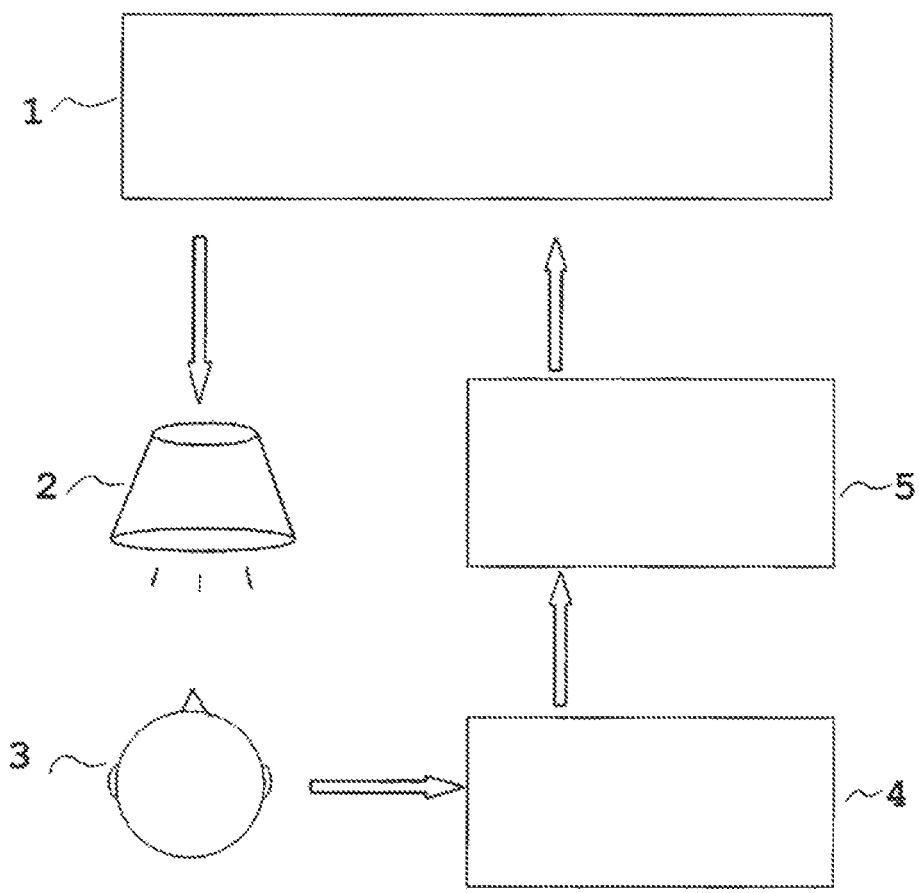

METHOD FOR TESTING HEARING AIDS

BACKGROUND OF THE INVENTION

1. Field of the Invention:

The invention relates to a method for testing speech comprehension of a person assisted by a hearing aid.

Hearing aids can help a person with diminished hearing perception compared with a person with normal hearing to perceive his/her environment in the same way as the person with normal hearing. However this is only possible with a high-quality hearing aid, which has to be adjusted precisely to the individual hearing loss of the person in question. It is particularly important for hearing-impaired people that they are able to converse with other people and therefore comprehend speech. It is therefore expedient and necessary to test the quality of a hearing aid and/or the quality of its adjustment in particular in respect of voice signals.

Hearing aids are already tested regularly during the development stage or after manufacture. Tests are also carried out in particular to determine the extent to which certain algorithms, for example for compression, frequency compression, noise interference suppression, etc., influence the ability of a person assisted by the hearing aid to comprehend speech. However speech comprehension tests can also be expediently carried out during or after hearing aid adjustment.

A method for testing and optimizing hearing aids is known from the publication US 2005/0027537 A1, in which a user assisted by a hearing aid is presented with meaningless syllables. Settable parameters of the hearing aid are reset as a function of whether the presented syllables are correctly understood.

BRIEF SUMMARY OF THE INVENTION

The object of the present invention is to improve a method for testing hearing aids, in particular in respect of their effect on speech comprehension.

This object is achieved by a method with the method steps as claimed.

A test system is provided to implement the method. The test system comprises a control unit for controlling the test. A meaningless word is first selected, preferably from a pool of stored meaningless words. The selected word is then presented to the person wearing the hearing aid (test subject) by way of an output medium, preferably a loudspeaker. A wired or wireless electrical signal transmission between the test system and the hearing aid is also possible however.

When assessing the quality of a hearing aid, the presentation of voice signals provides more reliable information compared with the presentation of sinusoidal tones. So that the hearing aid test can be performed internationally without modification, particularly language-independently, the voice signal presented preferably comprises meaningless syllables, referred to as logatomes. These can consist for example of vowel-consonant-vowel sequences (aba, aca, ada, . . . ) or consonant-vowel-consonant sequences (bab, beb, bib, . . . ). In some instances these meaningless syllables should be checked again and only those that have no meaning in all the major languages should be selected. The syllables presented preferably come from voice recordings, however they can also be synthetically generated.

A presented syllable (e.g. aba) is then displayed together with other similar-sounding syllables (e.g. ada, aga, aha, aka, . . . ) on a graphical user interface of the test system. The test subject selects the syllable he/she thinks he/she heard from the displayed syllables, for example using a pointer. Alternatively the test subject can repeat the syllable he/she identified and this can be captured by a speech recognition system.

The selection made is then evaluated. In the simplest instance the selection is identified as correct or incorrect.

The test is repeated with a new selection of meaningless syllables, until a termination criterion is reached.

According to the invention the acoustic voice signal is selected after each round as a function of at least one selection made by the test subject in response to a previously presented voice signal. The selection made by the test subject in response to the voice signal is therefore evaluated immediately after every round. The last selection and preferably also the results of previous rounds form part of the selection of a new voice signal, in particular a logatome. The selection of the voice signals (logatomes) is therefore adaptive, based on the "previous history". The adaptive selection of the voice signals from the voice signal pool constantly allows voice signals to be presented that are most likely to produce responses to the questions arising in the current test. Voice signals that are less suitable for the current test are passed over. This shortens the test time, since the test subject does not have to go through the entire inventory of voice signals (signal pool) for every test. The specific selection of voice signals and the gradual focusing of the voice signals during the ongoing test will detect and define the problem areas for the test subject in respect of speech comprehension, e.g. their ability to identify certain consonants correctly.

In one preferred embodiment of the invention an interference signal, in particular noise, is superimposed on the presented voice signal. When voice signals are presented in noise interference, the amplification setting of the hearing aid of the test subject has a secondary role. The test signals then only have to be presented at one volume, at which they can be clearly perceived. The sensitivity of the hearing test results from the variation of the signal to noise ratio SNR. The test starts initially with no or little noise component and the noise component is then increased progressively in each round in relation to the voice component, until the test subject no longer identifies the voice signal correctly.

The ratio of voice signal to interference signal, at which the test subject no longer identifies the voice signal, then allows reliable information to be derived about how good the hearing capacity of the test subject is with a hearing aid and therefore the quality of the hearing aid or assistance.

The reliability of the hearing aid test or the information it provides can be further improved by using fluctuating noise, in particular amplitude-modulated noise with a preferably random modulation, as the interference signal. The use of modulated noise interference provides a high level of sensitivity in respect of a hearing reduction, since the threshold for modulated sound is raised significantly for inner ear hearing problems in particular compared with normal hearing.

Particularly reliable and good results are also achieved if the voice signal is presented in each instance in the region of a minimum fluctuating interference signal.

In one embodiment of the invention not only the voice signals per se but also the response alternatives presented in response to a voice signal are adjusted adaptively to the test pattern to date. In this process the degree of similarity of the presented alternatives to the correct solution can vary. On the one hand therefore alternatives can be presented which have a high degree of similarity and on the other hand alternatives can be presented which have little similarity to the correct solution.

Like the selection of the voice signals, the selection of noise interference, the setting of the signal levels and in particular the level ratio between voice and noise interference and the timing of the voice signal in fluctuating noise are also effected adaptively, in other words as a function of the results of previous test rounds.

The inventive method can be used for a qualitative and quantitative determination of the improvement in speech comprehension as a result of the use of a hearing aid. It is also possible to perform a comparison between different hearing aids on the same test subject. Also different settings of the same hearing aid can be tested for their influence on speech comprehension, for example the influence of a compression, a frequency compression or a noise interference elimination algorithm.

BRIEF DESCRIPTION OF THE DRAWING

The invention is described in more detail below with reference to a flow diagram. The FIGURE shows the different stations for the performance of a hearing aid test according to the invention.

DETAILED DESCRIPTION OF THE INVENTION

First a logatome is selected randomly from a pool of logatomes 1 and presented by way of a loudspeaker 2 to a test subject 3 assisted by a hearing aid. The test subject is also shown the acoustically presented logatome together with similar logatomes on a display 4 for selection purposes. The test subject selects from the logatomes presented on the display the logatome he/she thinks was presented acoustically. The test subject's selection is first analyzed in an analysis and selection facility 5, in particular to determine whether the selection was correct. Depending on the result of the analysis, a new logatome is then specifically selected and presented to the test subject. This closes the circle and the method is continued until a termination criterion is reached.

The invention claimed is:

1. A method for testing speech comprehension of a person assisted by a hearing aid, which comprises the following steps of:
 a) providing a test system;
 b) selecting and presenting an acoustic voice signal in a form of at least one meaningless syllable and superimposing a fluctuating interference signal on the acoustic voice signal, the acoustic voice signal being presented in a region of a minimum fluctuating noise interference;
 c) displaying the meaningless syllable and a number of further meaningless syllables on a graphical user interface of the test system;
 d) selecting, via the person, a heard meaningless syllable from displayed meaningless syllables;
 e) evaluating a selection made; and
 f) repeating the method steps c) to e) until a termination criterion is reached, the selection of the acoustic voice signal being made in each instance in dependence on at least one selection made by the person in response to a previously presented voice signal.

2. The method according to claim 1, which further comprises performing at least one of a selection or a presentation of at least one of the acoustic voice signal or of the interference signal to repeat the method steps c) to f) in dependence on an evaluation of the selection made by the person in relation to at least one previous round of the method steps c) to f).

3. The method according to claim 2, which further comprises adjusting a signal to noise ratio between the acoustic voice signal and the interference signal.

4. The method according to claim 1, which further comprises adjusting a degree of similarity between the meaningless syllable selected and the further meaningless syllables.

5. The method according to claim 1, which further comprises using noise as the interference signal.

* * * * *